United States Patent

Rossi et al.

[11] Patent Number: 5,817,806
[45] Date of Patent: Oct. 6, 1998

[54] PROCESS FOR THE PREPARATION OF CYCLOHEXYL-AZETIDINONES

[75] Inventors: Tino Rossi; Paola Zarantonello; John Russel Thomas, all of Verona, Italy

[73] Assignee: Glaxo Wellcome SpA, Italy

[21] Appl. No.: 704,758

[22] PCT Filed: Mar. 23, 1995

[86] PCT No.: PCT/EP95/01114

§ 371 Date: Jan. 3, 1997

§ 102(e) Date: Jan. 3, 1997

[87] PCT Pub. No.: WO95/26333

PCT Pub. Date: Oct. 5, 1995

[30] Foreign Application Priority Data

Mar. 26, 1994 [GB] United Kingdom ............... 9406074

[51] Int. Cl.⁶ .................... C07D 205/08; C07F 7/18
[52] U.S. Cl. .......................................... 540/200
[58] Field of Search ............................. 540/200

[56] References Cited

FOREIGN PATENT DOCUMENTS

| 0 416 952 | 3/1991 | European Pat. Off. . |
| 0 422 596 | 4/1991 | European Pat. Off. . |
| 0 502 464 | 9/1992 | European Pat. Off. . |
| 94 21638 | 9/1994 | WIPO . |

Primary Examiner—Mark L. Berch
Attorney, Agent, or Firm—Bacon & Thomas

[57] ABSTRACT

1. A process for the preparation of compounds of formula (I) wherein $R_1$ is a hydroxyl protecting group

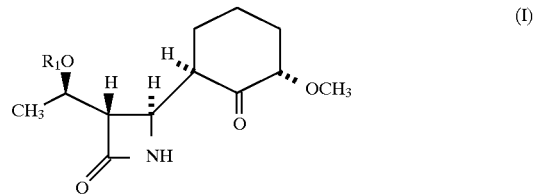

which comprises reacting the azetidinone (II) with the homochiral (2S)-2- methoxycyclohexane (III) or the complex thereof formed with one molecule of stannic chloide.

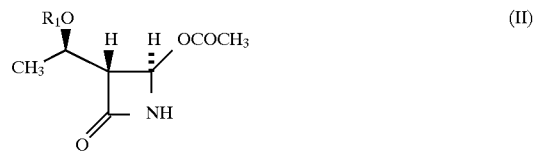

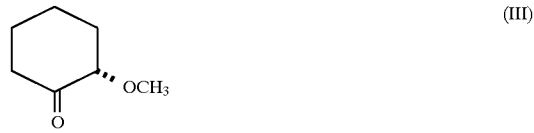

17 Claims, No Drawings

PROCESS FOR THE PREPARATION OF CYCLOHEXYL-AZETIDINONES

The present invention relates to an improved process for the preparation of cyclohexane derivatives useful in the preparation of antibacterial agents.

European Patent Application, publication No. 0416953A2 describes a novel class of tricyclic antibacterial agents. A particularly preferred compound described and claimed therein is the compound (A)

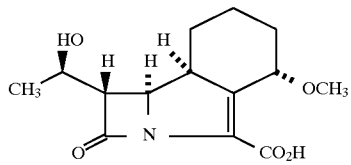

and salts thereof.

A key intermediate in the synthesis of compound (A) is the cyclohexane derivative (I).

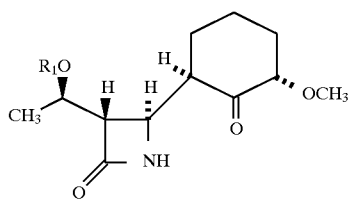

wherein $R_1$ is a hydroxyl protecting group such as trialkyl-silyl group e.g. t-bulydimethylsilyl.

The present invention provides a process for preparing the compounds of formula (I) in good yield and a high degree of enantiomeric purity.

Thus the present invention provides a process for the preparation of compounds of formula (I)

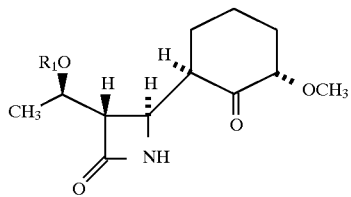

wherein $R_1$ is a hydroxyl protecting group which comprises reacting of the azetidinone (II) wherein $R_1$ is a hydroxyl protecting group.

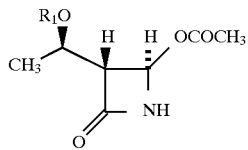

with the homochiral (2S)-2-methoxycyclohexanone (III) or the complex thereof formed with one molecule of stannic chloride

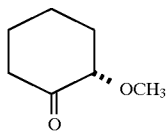

in an aprotic solvent and in the presence of a sterically hindered amine and a Lewis Acid.

Examples of suitable aprotic solvents for use in the reaction include halohydrocarbons such as dichloromethane, chlorobenzene or fluorobenzene. Other aprotic solvents that may be used in the reaction include aromatic hydrocarbons such as toluene, esters such as ethyl acetate or isopropyl acetate, or ethers such as 1–2 dimethoxyethane.

Suitable sterically hindered amines include tertiary amines and heterocyclic amines in which one or both of the carbon atoms attached to the nitrogen atom therein are substituted by one or two $C_{1-4}$ straight or branched chain alkyl groups.

Examples of suitable sterically hindered tertiary amines include tri $C_{1-6}$ straight or branched alkylamines (e.g. triethylamine, diisopropylethylamine, tri-isopropylamine or tri-isobutylamine), or tertiary aralkylamines (e.g. dibenzylethylamine, dibenzylmethylamine or N,N-dimethylbenzylamine).

Examples of suitable sterically hindered heterocyclic amines include αsubstituted pyrrolidines or piperidines e.g. 2,5-dimethylpyrrolidine, 2,6-dimethylpiperidine, 2,2,6,6-tetramethylpiperidine or αsubstituted aromatic heterocyclic amines such as 2,6-diterbutylpyridine or 2,6-dimethylpyridine.

Particularly convenient sterically hindered amines for use in the reaction include diisopropylethylamine, tri-isopropylamine, tri-isobutylamine, or 2,6-dimethylpyridine and more especially diisopropylethylamine.

Examples of suitable Lewes acids for use in the reaction include stannic chloride and stannic bromide. A particularly convenient Lewis acid for use in the reaction is stannic chloride.

Conveniently the reaction is carried out at a temperature within the range −30° to 20° e.g. −20° to 10° and more particularly −10° to 50°

In a preferred embodiment of this process the azetidinone (II) is added to a mixture of the compound (III) with the Lewis acid, optionally containing a small amount of the sterically hindered amine followed by addition of the sterically hindered amine.

The hydroxyl protecting group $R_1$, is preferably a trialkyl-silyl group such as a tri($C_{1-4}$)alkyl silyl group. Examples of suitable trialkylsilyl groups include trimethylsilyl and t-butyidimethylsilyl.

In a preferred embodiment of the invention the reaction is preferably carried out with an azetidinone of formula (II) wherein $R_1$ is a t-butyldimethylsilyl group.

The (2S)-2-methoxycyclohexanone (III) may be prepared by oxidation of (1S,2S)-2-methoxycyclohexanol using conventional procedures. Thus for example the oxidation may be carried out using oxalyl chloride and dimethylsulphoxide, pyridine/sulphur trioxide, sodium hypochlorite, N-bromacetamide 1,3-dibromo-5,5-dimethyl-hydantoin or Jones reagent ($CrO_3/H_2SO_4$). The reaction is conveniently carried out in a solvent, the choice of which will depend upon the oxidants to be used. Thus oxidation using oxalyl-chloride and dimethylsulphoxide is conveniently carried out in a halohydrocarbon e.g. dichloromethane and at a temperature within the range −78°–50°. Oxidation using pyridine and sulphur trioxide is conveniently carried out in a solvent such as an ether e.g. t-butylmethyl ether and in the presence of acetone and a base such as triethylamine or diisopyropylethylamine.

The oxidation using sodium hypochloride is conveniently carried out in the presence of 2,2,6,6-tetramethyl-1-piperidinyloxy and in a solvent system such as dichloromethane and water. Alternatively the oxidation with sodium hypochlorite may be carried out in the presence of a phase transfer catalyst.

The (2S)-2-methoxycyclohexanone may be isolated from the reaction mixture in the form of a 1 to 1 complex with stannic chlorride which may be formed by the subsequent addition of stannic chloride. Alternatively the stannic chloride complex with (2S)-2-methoxycyclohexanone may be prepared by addition of stannic chloride to a solution of (2S)-2-methoxycyclohexanone in a suitable solvent such as halohydrocabon e.g. chlorobenzene or toluene. Conveniently the reaction is carried out at a temperature between −20°–0° C. (1S,2S)-2-methoxycyclohexanol is a known compound and may be prepared using known procedures such as those described by Honig H, Senfer-Wassenthal P, Synthesis 1990, 1137–1140 Laumen K et al, J Chem. Soc., Chem. Commun., 1989, 148–150 or Peterson et al, Jorg. Chem, 1988, 53 1903–1907.

Alternatively the required (1 S,2S)-2-methoxycyclohexanol may be obtained from (±)-trans-2-methoxycyclohexanol by selective enzymic esterification of the unwanted (1R,2R) enantiomer using a suitable lipase and an acyl donor such as an anhydride or optionally substituted ethenyl ester followed by separation of the required alcohol from the unwanted ester using conventional means. This novel and advantageous process for preparing (1S,2S)-2-methoxycyclohexanol represents yet a further aspect of the invention.

Suitable lipases for use in the reaction, which may be readily determined by performing small scale experiments and measuring the extent of resolution in each case, preferably by means of a chiral chromatographic assay, include the lipases from Pseudomonas sp. and Candida antarctica. Preferably these are used in an immobilised form.

Lipases may be immobilised onto various solid supports by methods well known in the literature (e.g. Malcata et.al., J.Am.Oil Chem.Soc. 67 (12) pp 890–909, 1990). For example, lipases from Pseudomonas sp. may be conveniently immobilised by deposition onto a solid support such as a styrene-divinylbenzene copolymer resin e.g. Amberlite XAD-2 or a diatomaceous earth e.g. Dikalite, Celite. Immobilisation may be conveniently achieved by making slurries of enzyme and support in an aqueous buffer such as a solution of an inorganic phosphate salt e.g. ammonium dihydrogen orthophosphate in water, then removing water either by freeze drying or by adding suitable quantities of organic solvents which form azeotropic mixtures with water and concentrating mixtures under vacuum. Organic solvents for use in this azeotropic technique include alcohols e.g. butan-1-ol and hydrocarbons e.g. cyclohexane. Lipases may also be obtained from commercial suppliers in an immobilised form, for example Novozyme 435 (Novo-Nordisk Ltd.) which is an immobilised reparation of Candida antarctica lipase.

Suitable acyl donors for use in this process include acid anhydrides e.g. acetic anhydride, succinic anhydride, or more preferably an optionally substituted ethenyl ester such as the vinyl or isopropenyl esters of $C_{1-6}$ alkanoic acids e.g. vinyl acetate, vinyl propionate, vinyl butyrate, isopropenyl acetate or isopropenyl butyrate. The reaction is preferably carried out in an organic solvent such as an ether e.g. tetrahydrofuran, a nitrile e.g. acetonitrile or a hydrocarbon e.g. cyclohexane or dichloromethane and optionally in the presence of a tertiary organic base such as triethylamine. The substrate is present in reaction mixtures preferably at a concentration between 2 and 25% v/v, the acyl donor at a level of between 2 and 10 mol equivalents per mol racemic substrate, the tertiary organic base at a concentration between 0.1 and 5% v/v, and the immobilised enzyme preparation at a concentration between 1 and 30% w/v.

The required (1S,2S)-2-methoxycyclohexanol may be isolated from the reaction by conventional procedures such as column/flash chromatography or more preferably by a selective extraction procedure. Thus for example if the reaction is carried out in cyclohexane the product may be selectively extracted into water. Optionally a cyclohexane backwash may be performed to remove traces of the unwanted ester which partition into water. The product may then either be adsorbed onto a hydrophobic polymer resin such as a styrene-divinylbenzene copolymer e.g. Amberlite XAD-16 and eluted with a polar water miscible organic solvent such as acetone, or more preferably be back-extracted into an organic solvent such as ethyl acetate or dichloromethane which may be concentrated to give the required product. An inorganic salt such as sodium chloride may be added prior to back-extraction to enhance the efficiency of partitioning of the product into organic solvent.

In order that the invention may be more fully understood the following examples are given by way of illustration only.

In the examples all temperatures refer to ° C. Dried refers to solutions dried over anhydrous sodium sulphate.

EXAMPLE 1

(1S,2S)-2-methoxycyclohexanol

Method A

To a solution of (±) trans 2-methoxycyclohexanol (51 g) in dry tetrahydrofuran (1l), vinyl acetate (255 ml) and triethylamine (40.8 ml) were added. Psaeudomonas fluorescens lipase (8.5 g) was added and the suspension stirred under nitrogen for 5 day. The reaction was filtered on a paper filter and the organic phase evaporated under reduced pressure. The residue was purified by flash chromatography (petroleum ether:ether1:2) to give the title compound as a colourless oil (21.8 g). e.e +88% (shift reagent: tris(d,d-dicamphelylmethanane) Eu(III), $CDCl_3$)

Method B

Immobilised Candida antarctica lipase (Novozyme 435;10 g) was added to a solution of (±) trans-2-methoxycyclohexanol (50 g), vinyl acetate (42 ml) and triethylamine (6 ml) in cyclohexane (167 ml). The mixture was stirred in a stoppered conical flask for 24 h at room temperature and then filtered through a number 3 sinter funnel under vacuum. The filter cake was washed with cyclohexane (100 ml). The filtrate (350 ml) was taken and vigourously extracted with water (4×180 ml). The combined water extracts (820 ml) were back extracted with cyclohexane (200 ml). The water layer was taken and sodium chloride (245 g to give 5 M) added. After dissolution, the salt solution (ca 900 ml) was extracted with ethyl acetate (2×450 ml) and the combined ethyl acetate extracts were reduced in vacuo to afford the title product as a pale yellow oil (17.5 g ee>99%).

EXAMPLE 2

(2S)-2-methoxycyclohexanone

Method A

To a cooled (−78°) solution of oxalyl chloride (8.1 ml) in dry dichloromethane (250 ml) under nitrogen a solution of dimethylsulphoxide (1 3.4 ml) in dry dichloromethane (40 ml) was added slowly. After 30 min at −78° a solution of (1S,2S)-2-methoxycyclohexanol (8.2 g) in dry dichloromethane (40ml) was added maintaining the temperature below −60°. After 30 min triethylamine (52.4 ml) was added and the reaction was kept at −40° under vigourous stirring for 1 hour. A saturated solution of ammonium chloride was added, the phases were separated and the organic layer was washed with ice-cold hydrochloric acid (2% solution), saturated hydrogen carbonate, and brine. The organic layer was dried and then evaporated under reduced pressure. The residue was purified by flash chromatography (cyclohexane:ethyl acetate 8:2) to give the title compound as a yellow oil (6.7 g). $^1$H-NMR (400 MHz; CDCI$_3$) 3.74-3.68(1 H, m) 3.41(3 H,s); 2.58-2.46(1 H,m) 2.34-2.19(2 H,m); 2.01-1.88(2 H,m); 1.80-1.58(3 H,m). e.e=84% (shift reagent: tris[3-(heptafluropropyl-hydroxymethylen)-d-camphorate] Eu(III), CDCI$_3$)

Method B

A solution of (1S,1S)-1-methoxy-cyclohexanol (g 3.5) in acetone (10 ml) was added dropwise in 20 min at room temperature to a stirred solution containing N-bromoacetamide (108 g) in acetone (20 ml) and water (10 ml). The internal temperature rose to 35°–40° and the yellow mixture became orange during that time. After 3 h 30 min the reaction mixture was poured into a 30% aqueous solution of sodium sulphite (150 ml) and the mixture salted with sodium chloride (10 g). The colourless mixture was extracted with of t-butylmethyl ether (1×100 ml+1×50 ml). The combined organic phases were dried over and concentrated under reduced pressure at room temperature to give the title compound as a pale yellow liquid (, e.e.=100%; ). $^1$H-NMR(400 MHz; CDCI3): 3.67(m,1 H); 3.37 (s, 3 H); 2.50( m , 1 H); 2,3-2,1(m,2 H); 2.0-1.8(m,2 H); 1.6(m,3 H).

Method C

Concentrated sulphuric acid (6.1 ml) was added to a solution of chromium trioxide (7 g) in water (50 ml) cooled to 0°. An aliquot of this solution (30 ml) was added dropwise over a few minutes to a solution of (1S,2S)-1-methoxy cyclohexanol (1.95 g) in dichloromethane (15 ml) cooled to 0°. The solution was vigorously stirred at 0° for 1 h and then quenched by addition of isopropyl alcohol (2.5 ml). The mixture was extracted with dichloromethane (3×50 ml); the combined extracts were washed with a saturated solution sodium bicarbonate (30 ml), then with brine (50 ml) and dried. The mixture was then filtered over celite; the solution was evaporated under reduced pressure at room temperature to give the title compound as a pale yellow liquid ( yield= 56%, e.e.=100%). $^1$H-NMR(400 MHz; CDCI3): 3.68(m,1 H);3.40(s,3 H); 2.50(m,1 H);2.22-2.1 8(m,2 H);2.0-1.8(m,2 H); 1.6(m,3 H).

Method D

To a solution of (1S, 2S)-methoxycyclohexanol (264 g), 2, 2, 6, 6, tetramethyl-1 -piperidinyl (6.3 g), potassium bromide (4.83 g) and sodium bicarbonate (31.66 g) in dichloromethane (1320 ml) and water (396 ml) was added dropwise over 3 to 4 hr at a 15% aqueous solution of sodium hypochlorite (1145 ml) under vigorous stirring at 0° to 10°. The mixture was stirred for 30 min, the two layers separated and the aqueous phase back extracted with dichloromethane (792 ml).

The combined dichloromethane phases were washed with a 10% w/v solution of sodium sulphite (528 ml), cooled to 0° to 5° and treated with isopropyl alcohol (8.2 ml) and 98% sulphuric acid (6.7 ml). After 10 minutes the mixture was allowed to warm to 100° over a further 15 minutes. The resultant mixture was washed with water (264 ml) , saturated sodium bicarbonate solution (792 ml) and water (2×792 ml). The solution was dried azeotropically at reflux using a Dean Stark apparatus and then concentrated by distillation to give the title compound as a 26.5% w/w solution in dichloromethane (852 g), which may be used directly in the subsequent condensation reaction.

EXAMPLE 3

(3S,4R)-3[(R)-1-(t-butyldimethylsilyloxy)-ethyl]-4-{(R)-2'-[(S)-6'-(2-methoxy)-1'-oxocvclohexyl]}-azetidin-2-one A solution of 2(S) 2-methoxycyclohexanone (4.089 g) and (3S,4R)-4-acetoxy-3[(R)-(t-butyldimethylsilyloxy) ethyl]azetidinone (4.63 g) in dichloromethane (140 ml) was prepared at −16°. Tin tetrachloride (14.3 g) was added dropwise via syringe at such a rate that the temperature was kept beetween −16° and −13°. The mixture was stirred for 10 minutes, then the temperature was increased to +3°. A solution of di-isopropylethylamine (5.33 g) dissolved in dichloromethane (40 ml) was added over 20 minutes. The reaction mixture was stirred for 10 minutes at +3°, then the reaction mixture was poured into 300 ml of a 1:1 mixture of sodium bicarbonate (saturated) and Rochelle's salt (saturated) and extracted into diethylether (500 ml) with vigorous stirring over 1 h. The organic layer was washed with saturated brine(150 ml), dried and the solvent removed to give an white solid (7.10 g). The crude solid was taken up in hot n-hexane (175 ml), filtered and the volume reduced to 75 ml. The resulting mixture was warmed to completely dissolve the solid. The resultant solution was cooled and stirred and the title compound was isolated by filtration as a white solid (3.03 g).

EXAMPLE 4

(3S,4R)-3[(R)-1-tert-butyldimethylsilyloxy)ethyl]-4[(R)-2'-[(S)6'-2-methoxy)-1'-oxocyclohexyl]-azetidin-2-one To a mixture of (3S,4R)-acetoxy-3[(R)-(t-butyldimethylsilyloxy)ethyl]azetidinone (1.0 g) and the 2-methoxycyclohexanone tin tetrachloride complex (1.6 g) was added anhydrous chlorobenzene (20 ml). The resulting suspension was cooled to −20°, with vigorous stirring, and to it added tin tetrachloride (0.9 ml) over 2 minutes. The reaction mixture was then warmed to 0° and to it added a solution of triisobutylamine (2.2 ml) in anhydrous dichloromethane (5 ml) via a teflon cannula over 20 minutes. The resulting solution was stirred for a further 40 minutes at 0° before pouring into a vigorously stirred mixture of saturated aqueous sodium potassium tartrate (75 ml) saturated sodium bicarbonate (75 ml) and ethyl acetate (100 ml). After stirring for 40 minutes the phases were separated and the organic layer washed with 5% citric acid solution (100 ml), saturated sodium bicarbonate solution (20 ml) and saturated brine (40 ml). The organic phase was then treated with sodium sulphate (30 g), filtered and the solvent removed to give the crude product as an off-white semi crystalline solid (1.37 g). A quantity of the crude product (1.28 g) was recrystallised from hexane to give the desired title compound (0.91 g). $^1$H-NMR(500 MHz; CDCI3) 5.77(1 H,sa); 4.19(1 H,m), 4.00(1 H,m); 3.58(1 H,m);3.29(3H,m) ; 3.10(1 H,m); 2.89(1 H,dd);2.23(1 H,m); 2.12(1 H,m); 2.01(1 H,m);1.70-1.52(3 H,m); 1.25(3 H,d); 0.88(9 H,s); 0.087(3 H,s); 0.07(3 H,s).

EXAMPLE 5

(3S,4R)-3[(R)-1-(tert-butyldimethylsilyloxy)ethyl]-4 [(R)-2'[(S)-6'-(2-methoxy)-1'-oxocyclohexyl]]-azetidin-2-one Tin tetrachloride (1.59 ml) was added to a solution of (3S,4R)-4-acetoxy-3-(R)-t-butyldimethylsilyloxy)ethyl azetidinone (1.115 g) and (2S)-2-methoxycyclohexanone (0.6 ml) in dry dichloromethane (40 ml), cooled to −20° under a nitrogen atmosphere. The mixture was allowed to warm to 0°, then a solution of triisobutylamine (2.52 ml) in dry dichloromethane (10 ml) was added over 20 minutes. The reaction was stirred at 0° for 1 h. Then, it was poured into a mixture of Rochelle salt (40 ml), satured sodium hydrogen carbonate solution (40 ml), ethyl acetate (40 ml) and diethyl ether (30 ml). The mixture was stirred for 1 h, then the layers were separated. The aqueous layer was extracted with further ethyl acetate (40 ml). The combined organic extracts were washed with a 0.5 M citric acid solution (40 ml), satured sodium hydrogen carbonate solution (40 ml) and brine (50 ml). The organic layer was dried and concentrated in vacuo to give the crude title compound as a white solid (1.67 g). This material (1.5 g) was crystallized from n-hexane to give the title compound as a white solid (0.55 g). $^1$H-NMR (CDCI$_3$): 5.78 (s, 1 H); 4.18 (m, 1 H); 3.99 (m,1 H); 3.56 (t, 1 H); 3.28 (s, 3 H); 3.09 (m, 1 H); 2.88 (dd, 1 H); 2.21 (m,1 H); 2.10 (m, 1 H); 1.99 (m, 1 H); 1.72-1.6 (m, 2 H); 1.58 (m, 1 H); 1.25 (d, 3 H); 0.87 (s, 9 H); 0.07 (s, 3 H); 0.06 (s, 3 H).

EXAMPLE 6

2S)-(2)-Methoxycyclohexanone-(IV)-tin tetrachloride 1:1 chelatecomplex

To a stirred solution of (2S)-methoxycyclohexanone (2.0 ml) in dry chlorobenzene (15 ml) which had been cooled to −5° in an ice/salt bath was added tin tetrachloride (2.0 ml) at a rate sufficient to maintain the temperature below 0°. The resulting suspension was stirred for a further 15 minutes prior to filtering at the pump. The filter cake was washed with hexane (30 ml) and dried in vacuo to give the title compound (5.9 g) as a white-pale pink solid. m.p. 162°–165° C. (dec) $[\alpha_D]_{=}$−15.1° (c=0.935 in CH$_2$CI$_2$) IR (Nujol) n$_{max}$ 1649 cm$^{-1}$ NMR (CDCI$_3$); 4.12 (s, 1 H), 3.74 (s, 3 H), 2.78 (m, 1 H), 2.50 (m, 2 H), 2.16 (m,1 H), 2.1 -1.7 (m, 4 H)

EXAMPLE 7

(2S)-2-methoxy-cyclohexanone-Tin(IV) tetrachloride 1:1 chelate-complex 2,2,6,6,-tetramethyl-1-piperidineoxyl (288 mg), potassium bromide (225 mg) and water (24 ml) were added to a solution of (1S,2S)-2-methoxy-cyclohexanol (assay=91.2%, e.e.=100%) (8 g) in dichloromethane (80 ml). This mixture was cooled to 0° vigorously stirred and then a 13% solution of sodium hypochlorite (40 ml) buffered with sodium bicarbonate (680 mg) was added dropwise in 2 h 30 min. The mixture was additionally stirred for 30 min at 0°. The organic layer was separated and the aqueous layer extracted with dichloromethane (80 ml). Combined extracts were vigorously stirred for 1 h with of a satured solution sodium sulphite (32 ml). The organic layer was separated and the aqueous layer extracted with dichloromethane (20 ml). The combined extracts were washed with aqueous 30% citric acid (7.2 ml), then with a solution containing brine (10 ml) and 10% aqueous sodium bicarbonate (10 ml), dried and concentrated under vacuum to give (2S)-2-methoxychclohexane (9.415 mg) as a red liquid e.e.=100%).

Stannic chloride neat (8 ml) was slowly added to a solution of the (2S)-2-methoxy-cyclohexanone (8.63 g) in toluene (85 ml) at −5°/.0°; a precipitate formed. This mixture was stirred for 30 min at −5°. The precipitate was removed by filtration, washed with toluene (20 ml) and cold n-hexane (40 ml) and dried under vacuum overnight to give the title compound 16.43 g of a pale brown solid (decomposition temperature=118°–123°). $^1$H-NMR(400 MHz; CDCI3) 4.60 (m, 1 H); 4.04 (s, 3 H); 3.01 (m, 1 H); 2.8 (m,2 H);2.38 (m, 1 H );2.18 (m, 2 H); 20-1.78 (m, 2 H)

EXAMPLE 8

(3S,4R)-3-[(R)-1-(tert-butyldimethylsilyloxy)ethyl]-4-[(R)-2'-[(S)-6'-(2-methoxy)-1'-oxocvclohexy]]-azetidin-2one To a mixture of (3S,4R)-4-acetoxy-3-(R)-t-butyldimethylsilyloxy)ethyl azetidinone (1.0 g) and the compound of Example 6 (1.6 g) was added anhydrous dichloromethane (25 ml). The resulting suspension was cooled to −20° and to it added tin tetrachloride (0.9 ml) over 2 minutes. The reaction mixture was then warmed to 0° and to it added a solution of triisobutylamine (2.2 ml) in anhydrous dichloromethane (5 ml) via teflon cannula over 20 minutes. The resulting solution was stirred for a further 40 minutes at 0° before pouring into a vigorously stirred mixture of saturated aqueous sodium potassium tartrate (75 ml) saturated sodium bicarbonate (75 ml) and ethyl acetate (200 ml). After stirring for 20 minutes the phases were separated and the organic layer washed with 3% citric acid solution (100 ml), saturated sodium bicarbonate solution (50 ml) and brine (50 ml). The organic phase was then dried and concentrated in vacuo to give the crude title compound as an off-white semi crystalline gum (1.8 g). This material (1.7 g) was recrystallised from n-hexane to give the pure title compound (0.51 g). 1H-NMR (CDCI$_3$): 5.75 (s, 1 H); 4.18 (m.1 H); 3.99 (m, 1 H); 3.57 (t, 1 H); 3.28 (s,3 H); 3.09 (m, 1 H); 2.88 (m, 1 H); 2.23 (m, 1 H); 2.10 (m, 1 H); 1.99 (m, 1 H); 1.74-1.6 (m, 2 H); 1.58 (m,1 H); 1.25 (d, 3 H); 0.87 (s, 9 H); 0.08 (s, 3 H); 0.06 (s, 3 H).

EXAMPLE 9

(3S,4R)-3-[(R)-1(t-butyldimethylsilyloxy)ethyl]-4[(R)-2'-(S)-6'-methoxy-1'-oxocyclohexyl)azetidin-2-one Neat stannic chloride (55.2 ml) over 30 min at −5° and then diisopropylethylamine (6.4 ml.) over few minutes were dropped to a stirred solution of (2S)-2-Methoxycyclohexanone (22.56 ml) in dry dichloromethane (200 ml). To the resultant white suspension obtained a solution of (3S,4R)-4 -acetoxy-3-butyldimethylsilyloxyethyl-2-azetidinone (40 g) in dry dichloromethane (80 ml) over 15 minutes. The reaction temperature was allowed to rise to 0° and a solution of diisopropylethylamine (56.8 ml) in dry dichloromethane(80 ml) was added dropwise over 40 minutes. After further 15 minutes stirring the reaction mixture is poured into a chilled (0°) aqueous solution of 2N HCI and left under stirring for 15 minutes. After separation the organic layer was washed with 2N HCI (13×200 ml) and then stirred with a aqueous mixture of 20% w/v sodium, potassium tartrate/ 2M sodium carbonate (200 ml/120 ml) for 15 minutes. After separation the organic phase was washed with brine (200 ml), dried over sodium sulphate and the solvent evaporated under vacuum to give of the crude title compound 53 g as a whitish solid.

The crystallisation from n-hexane (600 ml) gave of pure title compound 35.15 g as a white solid. $^1$H-NMR(CDCI$_3$): 5.76(bs,1 H), 4.18(m,1 H), 3.99(m,1 H), 3.58(m,1 H), 3.28 (s,3 H), 3.09(m,1 H), 2.88(dd, 1 H), 2.25(m,1 H), 2.2-1.85 (m,2 H), 1.8-1.52(m,3 H), 1.26(d,3 H), 0.88(s,9 H), 0.087 (s,3 H), 0.07(s,3 H).

EXAMPLE 10

(3S,4R)-3-[(R)-1(t-butyldimethylsilyloxy)ethyl]-4[(R)-2'(S)-6'-methoxy-1'-oxocyclohexyl)azetidin-2-one Tin tetrachloride (55.6 ml) was added to a stirred solution of 2(S)-methoxycyclohexane (21.4 g) in anhydrous dichloromethane (220 ml) under nitrogen over 40 minutes at below −5°. The mixture was aged at −5° for 5 minutes then a solution of (3S, 4R)-4-acetoxy-3-(R)-to-butyldimethylsilyloxyethyl azetidinone (40 g) in anhydrous dichloromethane (100 ml) was added to the reaction mixture in under 20 min, keeping the temperature below −5°. Di-isopropylethylamine (63.1 ml) was added dropwise over 1 h keeping the temperature between 0° and 5° (the temperature over the first quarter of the addition was allowed to rise ca. 0°). The reaction was stirred at 0° to 5° C. for 10 min, then quenched by addition of the reaction mixture into a chilled (0°–50°) solution of 2 M hydrochloric acid (400 ml). The solution was stirred for 15 mins, and the organic phase then separated. The organic phase was washed three times with 2 M hydrochloric acid (3×200 ml) and then stirred with 20% w/v Rochelle's salt: 2 N sodium carbonate (5:3) (300 ml) for 30 min. The aqueous phase was backwashed with dichloromethane (80 ml), the combined organic phase were washed with 20% w/v aqueous brine (200 ml), and the aqueous phase again backwashed with dichloromethane (80 ml).

The organic solution was dried over magnesium sulphate, concentrated to dryness and the residue dissolved in dichloromethane (3); iso-octane (7) (280 ml) and the mixture was filtered through a 1 micron filter. The filter was washed with dichloromethane; iso-octane (0.45: 1.55) (100 ml) and the combined filtrates were further evaporated to dryness. The residue was dissolved in iso-octane (360 ml) at reflux. The solution was allowed to cool with stirring to 18°–22° overnight and the crystallised mixture was aged for a further 6 h at 0°–5°. The product was isolated by filtration, washed with iso-octane (2×100 in vacuo at 30° to give the title compound as a white yellow crystalline solid (32.7 g).

We claim:

1. A process for the preparation of compounds of formula (I):

where $R_1$ . is a hydroxy protecting group;
which comprises reacting an azetidinone of formula (II):

wherein $R_1$ is a hydroxy protecting group;

with a homochiral (2S)-2-methoxycyclohexanone of formula (III):

or a complex thereof formed with one molecule of stannic chloride, in an aprotic solvent and in the presence of a Lewis acid and a sterically hindered amine, which is a tri-$C_{1-6}$ straight or branched alkylamine. a tertiary benzylamine containing one or two benzyl groups and one or two $C_{1-6}$ alkyl groups substituted on the amine nitrogen atom or a heterocyclic amine which is pyrrolidine, piperidine or pyridine and in which one or both of the carbon atoms attached to the nitrogen atom therein are substituted by one or two $C_{1-4}$ straight or branched chain alkyl groups.

2. A process as claimed in claim 1 wherein the Lewis acid is stannic chloride.

3. A process as claimed in claim 1 wherein the sterically hindered amine is a compound selected from triethylamine di-isopropylethylamine, tri-isopropylamine, tri-isobutylamine, dibenzylethylamine, dibenzylmethylamine N,N-dimethylbenzlamine, 2,6-dimethylpiperidine, 2,2,6,6-tetramethylpiperidine, 2,6-diterbutylpyridine, or 2,6-dimethylpyridine.

4. A process as claimed in claim 3 wherein the sterically hindered amine is di-isopropylethylamine.

5. A process as claimed in claims 1 wherein the reaction is carried out at temperature within the range −20° to 10° C.

6. A process as claimed in claims 1 wherein the aprotic solvent is dichloromethane.

7. A process as claimed in claims 1 wherein the hydroxy protecting group $R_1$ is a t-butyldimethylsilyl group.

8. A process as claimed in claim 1 wherein the azetidinone (II) in which $R_1$ is a t-butyldimethylsilyl group is reacted with the homochiral (2S)-2 -methoxycyclohexanane (III) in the presence of stannic chloride and a sterically hindered amine.

9. A process as claimed in claim 8 wherein the sterically hindered amine is di-isopropylethylamine.

10. A process as claimed in claims 1 wherein the azetidinone (II) is added to a mixture of the Lewis acid, and homochiral 2-methoxycyclohexanone (III), followed by addition of the sterically hindered amine.

11. A process as claimed in claim 9 wherein the temperature is within the range of −10° to 5° C.

12. A process as claimed in claim 2 wherein the hydroxy protecting group $R_1$ is a t-butyldimethylsilyl group.

13. A process as claimed in claim 3 wherein the hydroxy protecting group $R_1$ is a t-butyidimethylsilyl group.

14. A process as claimed in claim 4 wherein the hydroxy protecting group $R_1$ is a t-butyidimethylsilyl group.

15. A process as claimed in claim 5 wherein the hydroxy protecting group $R_1$ is a t-butyldimethylsilyl group.

16. A process as claimed in claim 6 wherein the hydroxy protecting group $R_1$ is a t-butyldimethylsilyl group.

17. A process as claimed in claim 8 wherein the temperature is within the range of −10° to 5° C.

* * * * *